United States Patent
Yajima et al.

(10) Patent No.: US 9,067,857 B2
(45) Date of Patent: Jun. 30, 2015

(54) FLUORINE-CONTAINING AROMATIC COMPOUND AND MANUFACTURING METHOD THEREFOR

(71) Applicant: Asahi Glass Company, Limited, Chiyoda-ku, Tokyo (JP)

(72) Inventors: Tomoko Yajima, Tokyo (JP); Kyoko Yamamoto, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/459,025

(22) Filed: Aug. 13, 2014

(65) Prior Publication Data

US 2014/0357906 A1    Dec. 4, 2014

Related U.S. Application Data

(63) Continuation of application No. PCT/JP2013/053585, filed on Feb. 14, 2013.

(30) Foreign Application Priority Data

Feb. 17, 2012    (JP) ................................ 2012-033156

(51) Int. Cl.
| | | |
|---|---|---|
| C07C 17/32 | (2006.01) | |
| H01L 51/00 | (2006.01) | |
| C07C 17/361 | (2006.01) | |
| H01L 51/05 | (2006.01) | |

(52) U.S. Cl.
CPC ............ *C07C 17/32* (2013.01); *H01L 51/0052* (2013.01); *H01L 51/0055* (2013.01); *H01L 51/0058* (2013.01); *H01L 51/0558* (2013.01); *C07C 2103/24* (2013.01); *C07C 2103/52* (2013.01); *C07C 17/361* (2013.01)

(58) Field of Classification Search
CPC .. C07C 17/32; C07C 17/361; C07C 2103/24; C07C 2103/52; H01L 51/0055; H01L 51/0052; H01L 51/0058; H01L 51/0558
USPC ....................................................... 570/144
See application file for complete search history.

(56) References Cited

U.S. PATENT DOCUMENTS

| | | | |
|---|---|---|---|
| 3,271,441 A | | 9/1966 | Brace |
| 3,875,249 A | * | 4/1975 | Nelson ........................... 570/194 |
| 4,038,331 A | * | 7/1977 | Tobin ............................. 570/144 |
| 4,207,266 A | * | 6/1980 | Opie .............................. 570/144 |
| 2006/0273311 A1 | | 12/2006 | Ohe et al. |
| 2007/0215902 A1 | | 9/2007 | Nakagawa |
| 2009/0140241 A1 | | 6/2009 | Ohe et al. |
| 2009/0230387 A1 | | 9/2009 | Ohe et al. |
| 2012/0208989 A1 | | 8/2012 | Sun |

FOREIGN PATENT DOCUMENTS

| | | |
|---|---|---|
| JP | A-S52-075932 | 6/1977 |
| JP | A-H02-062832 | 3/1990 |
| JP | 2007-013097 A | 1/2007 |
| WO | WO-2006/019133 A1 | 2/2006 |
| WO | WO-2011/022678 A1 | 2/2011 |

OTHER PUBLICATIONS

Bravo, et al., "New Methods of Free-Radical Perfluoroalkylation of Aromatics and Alkenes. Absolute Rate Constants and Partial Rate Factors for the Homolytic Aromatic Substitution by n-Perfluorobutyl Radical," J. Org. Chem. 1997, vol. 62, p. 7128-7136.
Gundlach et al., "Thin-film transistors based on well-ordered thermally evaporated naphthacene films," Applied Physics Letters, vol. 80 No. 16, Apr. 22, 2002, p. 2925-2927.
International Search Report dated May 21, 2013 issued in Application No. PCT/JP2013/053585.
Kobayashi et al., "Studies on the Organic Fluorine Compounds. XXIV[1])Photochemical Trifluoromethylation of Aromatic Compounds[2])," Chem. Pharm. Bull., 1978, vol. 26, No. 4, p. 1247-1249.
Sun et al., "Arene Trifluoromethylation: An Effective Strategy to Obtain Air-Stable n-Type Organic Semiconductors with Tunable Optoelectronic and Electron Transfer Properties," The Journal of Physical Chemistry A, Jul. 10, 2012, vol. 116, No. 30, p. 8015-8022, Table 2, pentacene_6, 13-CF3.

* cited by examiner

*Primary Examiner* — Shailendra Kumar
(74) *Attorney, Agent, or Firm* — Foley & Lardner LLP

(57) ABSTRACT

A method of manufacturing a fluorine-containing aromatic compound represented by the following formula (2-1) or formula (2-2): [R is a hydrogen atom, an alkyl group having a carbon number of 1 to 12 which may have a substituent other than a fluorine atom, or a monovalent aromatic group which may have a substituent; $Rf_1$ and $Rf_2$ are a fluorine-containing alkyl group having a carbon number of 1 to 12 and $Rf_1$ and $Rf_2$ may be the same or different; and m is an integer of 1 or more, n is an integer of 0 or more and m+n is an integer of 1 or more and 5 or less].

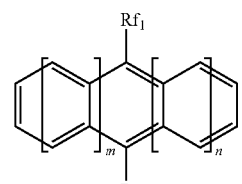

(2-1)

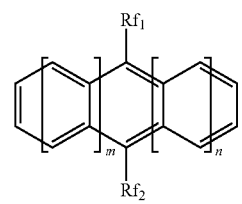

(2-2)

18 Claims, No Drawings

FLUORINE-CONTAINING AROMATIC COMPOUND AND MANUFACTURING METHOD THEREFOR

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/053585 filed on Feb. 14, 2013, which is based upon and claims the benefit of priority of Japanese Application No. 2012-033156 filed on Feb. 17, 2012, the entire contents of which are hereby incorporated by reference in their entireties.

TECHNICAL FIELD

The present invention relates to a novel fluorine-containing aromatic compound applicable to organic semiconductor materials and a manufacturing method thereof.

BACKGROUND ART

Since an organic semiconductor element using an organic compound as a semiconductor material exhibits easiness in workability as compared with conventional semiconductor elements using inorganic semiconductor materials such as silicon, it has been expected to realize a low-cost device. Moreover, since a semiconductor material of an organic compound is structurally flexible, it has been expected to realize a device such as a flexible display by using the material in combination with a plastic substrate.

As working processes for organic semiconductors, there is known a dry process by vapor deposition and a wet process using an organic solvent, such as coating, printable, or ink jet. Since a conventional organic semiconductor material has a low solubility in organic solvents and thus it is difficult to apply the wet process thereto, the dry process has been widely utilized. On the other hand, the wet process is easy and inexpensive and is a manufacturing process exhibiting a little environmental burden.

An improvement in carrier mobility is required for an organic semiconductor material. As a method of improving the carrier mobility of the organic semiconductor material, an effective method has not yet been established but it is considered to be important to strengthen intermolecular interaction or control arrangement of molecules. Since an acene compound that is a condensed polycyclic compound has an expanded conjugate system owing to its planar structure and has a strong intermolecular interaction owing to π stacking, it is attempted to utilize the compound as an organic semiconductor material (Non-Patent Document 1).

An acene compound is a compound having a skeleton in which benzene rings are linearly condensed. The acene compound has a small theoretical band gap as compared with polyacetylene and the like and thus an excellent function as an organic semiconductor material is expected and the function is expectable as the number of rings increases. Moreover, the compound has a possibility of changing conductivity depending on a substituent.

In an acene compound having no substituent, solubility in an organic solvent decreases as the number of the rings increases. Therefore, it is difficult to apply the wet process to the acene compound. Also, there is very narrow range for selecting solvent and temperature condition.

There is proposed an acene compound having an increased affinity to organic solvents and being applicable to the wet process, by introducing a substituent such as an alkyl group into the acene skeleton (Patent Document 1).

Patent Document 2 discloses a method for manufacturing an anthracene having a perfluoroalkyl group by a coupling reaction using a heavy metal. As the compound, an anthracene having $C_8F_{17}$-groups substituted at 6- and 13-positions is disclosed. Since the manufacturing method of Patent Document 2 uses a coupling reaction of a halo-substituted acene compound with a perfluoroalkyl iodide in the presence of a heavy metal (Cu), synthesis is vexatious and complicated. Moreover, an organic semiconductor material is required to be highly pure. Therefore, in the case of contamination with a heavy metal, much labor is necessary for ultra-high purification (sublimation purification etc.).

In order to avoid this problem, it is considered to apply direct polyfluoroalkylation to aromatics without using the heavy metal coupling reaction. There are reports of perfluoroalkylation to benzenes but there is hitherto no report of perfluoroalkylation to an acene compound (Patent Document 3 and Non-Patent Document 2).

PRIOR ART DOCUMENTS

Patent Documents

Patent Document 1: JP-A-2007-13097
Patent Document 2: WO2011/022678
Patent Document 3: U.S. Pat. No. 3,271,441

Non-Patent Documents

Non-Patent Document 1: D. J. Gundlach, S. F. Nelson, T. N. Jachson et al., Appl. Phys. Lett., (2002), 80, 2925.
Non-Patent Document 2: Anna Bravo et al., J. Org. Chem., (1997), 62, 7128.

SUMMARY OF THE INVENTION

Problems that the Invention is to Solve

As mentioned above, conventional organic semiconductor materials expectable to exhibit high carrier mobility have a low solubility in solvents and are mainly obtained by a dry process. Further, it is proposed to obtain an anthracene having a polyfluoroalkyl group by a method using a heavy metal but there is a problem that the heavy metal remains.

The present invention provides a compound applicable to both of dry process and wet process and useful as an organic semiconductor material having high carrier mobility.

Specifically, provided is an acene compound which is soluble even in a low polar solvent and in which high carrier mobility is expectable resulting from a strong intermolecular interaction. Moreover, provided is an acene compound having a little contamination with heavy metals which is one cause of a decrease in carrier mobility, and a manufacturing method thereof.

Means for Solving the Problems

The present inventors have accomplished the present invention relating to a fluorine-containing aromatic compound having a specific structure, which has a little contamination with heavy metals and is soluble even in a low polar solvent, and a manufacturing method thereof.

That is, the present invention relates to the followings.

<1>
A fluorine-containing aromatic compound selected from a compound represented by the following formula (2-1) and a compound represented by the formula (2-2):

[Chem 1]

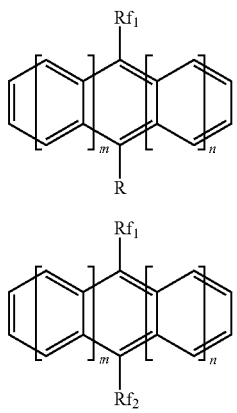

(2-1)

(2-2)

[R is a hydrogen atom, an alkyl group having a carbon number of 1 to 12 which may have a substituent, or a monovalent aromatic group which may have a substituent.

$Rf_1$ and $Rf_2$ are a fluorine-containing alkyl group having a carbon number of 1 to 12 which may have a substituent. $Rf_1$ and $Rf_2$ may be the same or different.

m is an integer of 1 or more, n is an integer of 0 or more and m+n is an integer of 1 or more and 5 or less, However, in the formula (2-2), the cases where $Rf_1$ and $Rf_2$ are both $CF_3$ and are both $nC_8F_{17}$ at the time of m=n=1 and the case where $Rf_1$ and $Rf_2$ are both $nC_8F_{17}$ at the time of m=n=2 are excluded.]

<2>
The fluorine-containing aromatic compound according to the above <1>, in which in the formula (2-1), $Rf_1$ is a perfluoroalkyl group having a carbon number of 1 to 6.

<3>
The fluorine-containing aromatic compound according to the above <1>, in which R is a hydrogen atom, an alkyl group having a carbon number of 2 to 12 which may have a substituent other than a fluorine atom, or a monovalent aromatic group which may have a substituent; and $Rf_1$ and $Rf_2$ may be the same or different, and $Rf_1$ is a fluorine-containing alkyl group having a carbon number of 1 to 12 which may have a substituent and $Rf_2$ is a fluorine-containing alkyl group having a carbon number of 4 to 7 which may have a substituent.

<4>
The fluorine-containing aromatic compound according to the above <1> or <2>, in which in the formula (2-2), $Rf_1$ and $Rf_2$ may be the same or different, and $Rf_1$ is a perfluoroalkyl group having a carbon number of 1 to 12 and $Rf_2$ is a perfluoroalkyl group having a carbon number of 4 to 7.

<5>
The fluorine-containing aromatic compound according to the above <1> or <3>, in which the compound represented by the formula (2-1) is a compound represented by the following formula (3-1) and the compound represented by the formula (2-2) is a compound represented by the following formula (3-2):

[Chem 2]

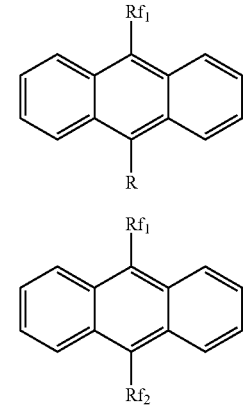

(3-1)

(3-2)

[$Rf_1$, $Rf_2$ and R represent the same meanings as mentioned above.]

<6>
The fluorine-containing aromatic compound according to the above <5>, in which in the formula (3-2), $Rf_1$ and $Rf_2$ may be the same or different, and $Rf_1$ is a perfluoroalkyl group having a carbon number of 1 to 12 and $Rf_2$ is a perfluoroalkyl group having a carbon number of 4 to 7.

<7>
The fluorine-containing aromatic compound according to the above <1> or <3>, in which the compound represented by the formula (2-1) is a compound represented by the following formula (4-1) and the compound represented by the formula (2-2) is a compound represented by the following formula (4-2):

[Chem 3]

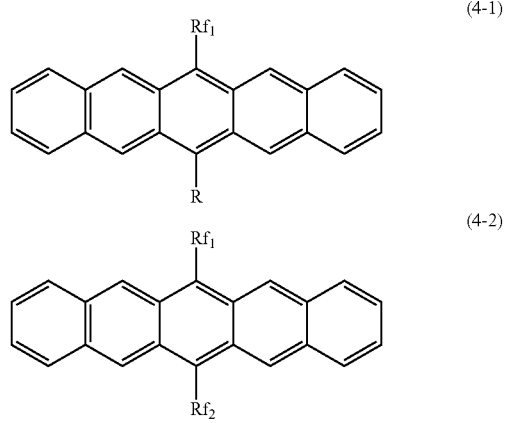

(4-1)

(4-2)

[$Rf_1$ and $Rf_2$ represent the same meanings as mentioned above.]

<8>
The fluorine-containing aromatic compound according to the above <7>, in which in the formula (4-2), $Rf_1$ and $Rf_2$ may be the same or different, and $Rf_1$ is a perfluoroalkyl group having a carbon number of 4 to 7 and $Rf_2$ is a perfluoroalkyl group having a carbon number of 1 to 12.

<9>
An organic semiconductor material containing the fluorine-containing aromatic compound described in any one of the above <1> to <8>.

<10>
An organic semiconductor thin film containing the organic semiconductor material described in the above <9>.
<11>
An organic semiconductor element containing a substrate and the organic semiconductor thin film described in the above <10>.
<12>
A transistor containing a gate electrode, a dielectric layer, a source electrode, a drain electrode, and a semiconductor layer, in which the semiconductor layer is composed of the organic semiconductor thin film described in the above <10>.
<13>
A method for manufacturing a fluorine-containing aromatic compound, the method including: reacting a compound represented by the following formula (1) with a compound represented by the formula $Rf_1X_1$ in a halogen-containing solvent in the presence of a thiosulfate salt under light irradiation and subsequently heating, thereby obtaining a fluorine-containing aromatic compound represented by the following formula (2-1):

[Chem 4]

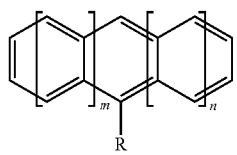
(1)

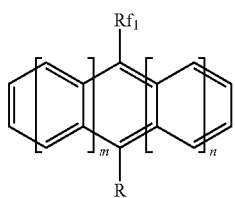
(2-1)

[R is a hydrogen atom, an alkyl group having a carbon number of 2 to 12 which may have a substituent other than a fluorine atom, or a monovalent aromatic group which may have a substituent.

$Rf_1$ is a fluorine-containing alkyl group having a carbon number of 1 to 12.

$X_1$ represents an iodine atom or a bromine atom.

m is an integer of 1 or more, n is an integer of 0 or more and m+n is an integer of 1 or more and 5 or less.]
<14>
A method for manufacturing a fluorine-containing aromatic compound represented by the following formula (2-2), the method including: reacting a compound represented by the following formula (1-1) with a compound represented by the formula $Rf_1X_1$ in a halogen-containing solvent in the presence of a thiosulfate salt under light irradiation to obtain a compound represented by the following formula (1-1'), subsequently heating the compound represented by the formula (1-1') to obtain a fluorine-containing aromatic compound represented by the following formula (2-1-1), then obtaining the compound represented by the formula (2-1-1), and subsequently reacting the compound represented by the formula (2-1-1) with a compound represented by the formula $Rf_2X_2$ in a halogen-containing solvent in the presence of a thiosulfate salt under light irradiation and heating:

[Chem 5]

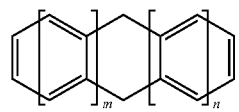
(1-1)

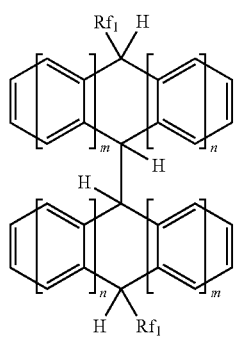
(1-1')

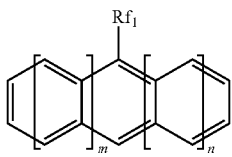
(2-1-1)

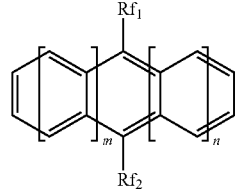
(2-2)

[$Rf_1$ and $Rf_2$ are a fluorine-containing alkyl group having a carbon number of 1 to 12 which may have a substituent. $Rf_1$ and $Rf_2$ may be the same or different.

$X_1$ and $X_2$ represent an iodine atom or a bromine atom and may be the same or different.

m is an integer of 1 or more, n is an integer of 0 or more and m+n is an integer of 1 or more and 5 or less.]
<15>
An organic semiconductor material containing the fluorine-containing aromatic compound described in any one of the above <1> to <8>, in which contents of metals of Ni, Cu, Zn, and Pd are each 1 ppm by mass or less and total content of the metals is 10 ppm by mass or less.
<16>
An organic semiconductor material containing at least one fluorine-containing aromatic compound selected from a compound represented by the following formula (2-1) and a compound represented by the following formula (2-2), in which contents of metals of Ni, Cu, Zn, and Pd are each 1 ppm by mass or less and total content of the metals is 10 ppm by mass or less:

[Chem 6]

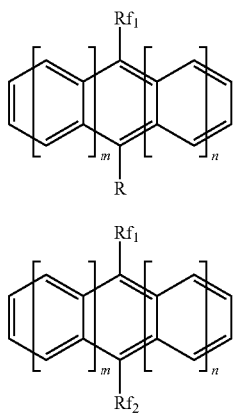

[R is a hydrogen atom, an alkyl group having a carbon number of 2 to 12 which may have a substituent other than a fluorine atom, or a monovalent aromatic group which may have a substituent.

$Rf_1$ and $Rf_2$ are a fluorine-containing alkyl group having a carbon number of 1 to 12 which may have a substituent. $Rf_1$ and $Rf_2$ may be the same or different.

m is an integer of 1 or more, n is an integer of 0 or more and m+n is an integer of 1 or more and 5 or less.]

<17>

A compound represented by the following formula (1-1'):

[Chem 7]

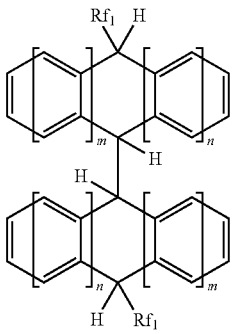

[$Rf_1$ is a fluorine-containing alkyl group having a carbon number of 1 to 12 which may have a substituent.

m is an integer of 1 or more, n is an integer of 0 or more and m+n is an integer of 1 or more and 5 or less.]

Advantageous Effects of the Invention

The fluorine-containing aromatic compound obtained by the manufacturing method of the present invention has a little possibility of contamination with heavy metals and has high carrier mobility as a charge-transporting material. Since a fluorine-containing substituent having a specific structure is introduced, the fluorine-containing aromatic compound is soluble in a low polar solvent and thus, an organic semiconductor thin film can be manufactured in large quantities conveniently for a short period of time by using a wet process such as application or an ink-jet method. Accordingly, the fluorine-containing aromatic compound of the present invention can be utilized as an organic semiconductor material applicable to high-performance organic TFTs, organic EL elements, and the like.

The carrier mobility in the present Description has a broad meaning including electron mobility and hole mobility.

MODES FOR CARRYING OUT THE INVENTION

The following will describe the present invention in detail but the present invention should not be construed as being limited to the following modes for carrying out the same and can be carried out with arbitrary modifications within the scope not deviating from the gist of the present invention.

In the Description, a compound represented by the formula (X) is also referred to as a "compound (X)".

<Fluorine-Containing Aromatic Compound>

The fluorine-containing aromatic compound of the present invention is a compound represented by the following formula (2-1) or a compound represented by the formula (2-2).

[Chem 8]

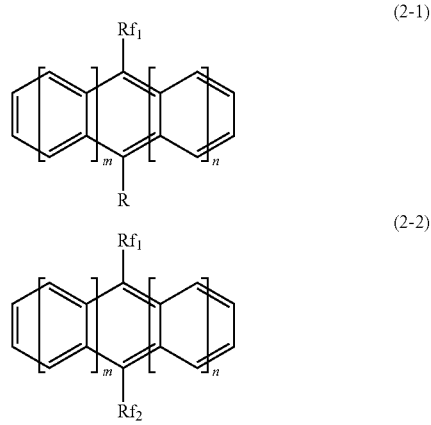

$Rf_1$ and $Rf_2$ are each independently a fluorine-containing alkyl group having a carbon number of 1 to 12 which may have a substituent. $Rf_1$ and $Rf_2$ may be the same or different. The fluorine-containing alkyl group means a group in which one or more hydrogen atom(s) of an alkyl group are replaced by fluorine atom(s).

In general, as the number of condensed rings increases, carrier mobility tends to increase owing to strong intermolecular interaction by π-π stacking. The fluorine-containing alkyl group in the fluorine-containing aromatic compound of the present invention further improves the solubility in an organic solvent. Moreover, the fluorine-containing alkyl group controls electron transition energy of an acene skeleton owing to an electron-withdrawing property thereof.

The fluorine-containing alkyl group is preferably a polyfluoroalkyl group having a total carbon number of 1 to 12 and is preferably a perfluoroalkyl group having a total carbon number of 1 to 12. The polyfluoroalkyl group means a group in which two or more hydrogen atoms in an alkyl group are replaced by fluorine atoms. The perfluoroalkyl group means a group in which all the hydrogen atoms in an alkyl group are replaced by fluorine atoms. The carbon skeleton of the fluorine-containing alkyl group is preferably linear one or branched one and is preferably linear one.

Moreover, in the case where $Rf_1$ and $Rf_2$ have a substituent, examples of the substituent include a bromine atom, an iodine atom, a nitrile group, a carboxyl group, and an ester group (acyloxy group or alkoxycarbonyl group).

$Rf_1$ and $Rf_2$ are preferably an unsubstituted group, i.e., a fluorine-containing alkyl group having a carbon number of 1 to 12. In view of good performance as an organic semiconductor and good yields, a polyfluoroalkyl group having a carbon number of 1 to 12 is particularly preferred and a perfluoroalkyl group having a carbon number of 1 to 12 is especially preferred. The carbon number of $Rf_1$ is preferably from 1 to 6. Furthermore, $Rf_1$ is preferably a polyfluoroalkyl group having a carbon number of 1 to 6, and particularly preferably a perfluoroalkyl group having a carbon number of 1 to 6. The carbon number of $Rf_2$ is preferably from 4 to 7. Moreover, $Rf_1$ and $Rf_2$ are preferably a group having a linear structure from the standpoint of performance as an organic semiconductor.

As $Rf_1$ and $Rf_2$, specifically, preferred is a trifluoromethyl group, a perfluoroethyl group, a perfluoropropyl group, a perfluoroisopropyl group, a perfluorobutyl group, a perfluoroisobutyl group, a perfluoro-sec-butyl group, a perfluoro-tert-butyl group, a perfluorohexyl group, a perfluoroheptyl group, or a perfluorooctyl group and, in view of solubility in an organic solvent, particularly preferred is a trifluoromethyl group, a perfluoroethyl group, a perfluoropropyl group, a perfluoroisopropyl group, a perfluorobutyl group, a perfluoroisobutyl group, a perfluoro-sec-butyl group, a perfluoro-tert-butyl group, or a perfluorohexyl group.

In the compound (2-1), R is a hydrogen atom, an alkyl group having a carbon number of 1 to 12 which may have a substituent, or a monovalent aromatic group which may have a substituent, and is preferably a hydrogen atom, an alkyl group which may have a substituent having a total carbon number of 2 to 12 other than a fluorine atom, or a monovalent aromatic group which may have a substituent.

The alkyl group is preferably a linear or branched alkyl group having a carbon number of 2 to 12 or a cycloalkyl group having a carbon number of 3 to 12 and, from the standpoint of improvement in solubility in an organic solvent, preferred is an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, or a dodecyl group.

As the substituent of R being an alkyl group, preferred is a substituent other than a fluorine atom and specifically includes a chlorine atom, a bromine atom, an amino group, a cyano group, and the like. The number of the substituents is not limited and is preferably 1.

Moreover, the monovalent aromatic group is preferably an unsubstituted monovalent aromatic group and a phenyl group and a thienyl group may be mentioned.

As the substituent of R being a monovalent aromatic group, an alkyl group, a nitro group, a cyano group, and the like may be mentioned. The number of the substituents is not limited and is preferably 1.

R is preferably a hydrogen atom or an unsubstituted alkyl group having a carbon number of 2 to 12.

In the compound (2-1) and the compound (2-2), m and n represent the numbers of repetitions of unit structures and m is an integer of 1 or more, n is an integer of 0 or more, and m+n is an integer of 1 or more and 5 or less. Preferably, m+n is 2 or 4.

Particularly, in the compound (2-1) and the compound (2-2), the case of m=n=1 or 2 is preferred. In the case of m=n=1, bonding positions of $Rf_1$ and $Rf_2$ are preferably 9-position and 10-position of the acene skeleton, respectively. Namely, the following compound (3-1) or compound (3-2) is preferred.

[Chem 9]

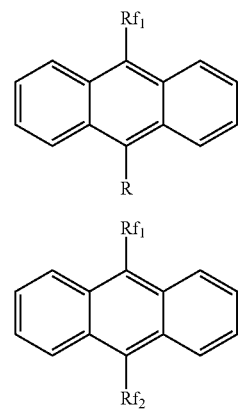

(3-1)

(3-2)

In the compound (3-1) and the compound (3-2), $Rf_1$, $Rf_2$ and R represent the same meanings as mentioned above. As $Rf_1$ and $Rf_2$, preferred is a polyfluoroalkyl group having a total carbon number of 1 to 12 which may have a substituent, and particularly preferred is a perfluoroalkyl group having a total carbon number of 1 to 12 which may have a substituent.

As $Rf_1$ in the compound (3-1), preferred is an unsubstituted group and is preferably a polyfluoroalkyl group having a carbon number of 1 to 12, particularly preferred is a perfluoroalkyl group having a carbon number of 1 to 12, and especially preferred is a perfluoroalkyl group having a linear structure and a carbon number of 1 to 12. The carbon number in $Rf_1$ is preferably from 1 to 6. $Rf_1$ is preferably one of these groups having a carbon number of 1 to 6.

$Rf_1$ and $Rf_2$ in the compound (3-2) may be the same or different and especially preferably, $Rf_1$ is a perfluoroalkyl group having a carbon number of 1 to 12 and $Rf_2$ is a perfluoroalkyl group having a carbon number of 4 to 7. These groups having linear structure are further preferred.

In the case of m=n=2, bonding positions of $Rf_1$ and $Rf_2$ are preferably 6-position and 13-position of the acene skeleton in the compound (2-1) or the compound (2-2), respectively. Namely, the following compound (4-1) or compound (4-2) is preferred.

[Chem 10]

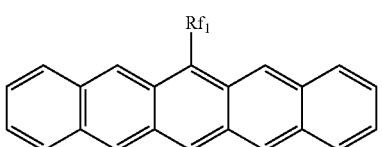

(4-1)

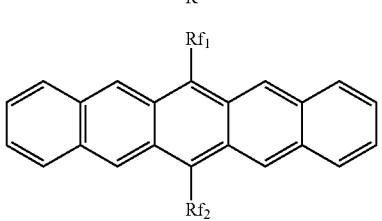

(4-2)

$Rf_1$, $Rf_2$ and R represent the same meanings as mentioned above. As $Rf_1$ and $Rf_2$, preferred is a polyfluoroalkyl group having a carbon number of 1 to 12 which may have a substituent, and particularly preferred is a perfluoroalkyl group having a carbon number of 1 to 12 which may have a substituent. Furthermore, an unsubstituted group is preferred as $Rf_1$ and $Rf_2$, and preferred is a polyfluoroalkyl group having a carbon number of 1 to 12 and particularly preferred is a perfluoroalkyl group having a carbon number of 1 to 12.

$Rf_1$ in the compound (4-1) is preferably a polyfluoroalkyl group having a carbon number of 1 to 12, particularly preferably a perfluoroalkyl group having a carbon number of 1 to 12, and especially preferably a perfluoroalkyl group having a linear structure and a carbon number of 1 to 12. The carbon number in $Rf_1$ is preferably from 1 to 6. $Rf_1$ is preferably one of these groups having a carbon number of 1 to 6.

Furthermore, the fluorine-containing aromatic compound of the present invention includes compounds selected from the compound group represented by the following formulae.

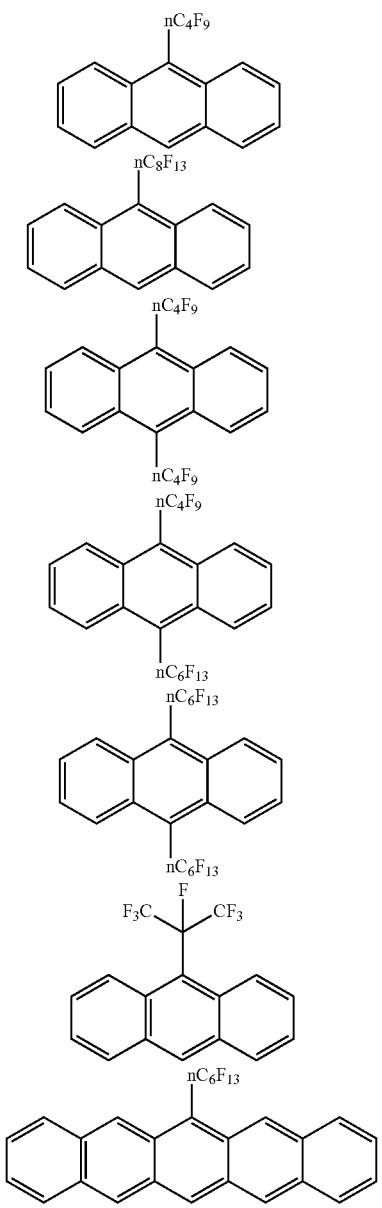

[Chem 11]

<Manufacturing Method of Fluorine-Containing Aromatic Compound>

The fluorine-containing aromatic compound of the present invention can be manufactured by a method (a) or a method (b).

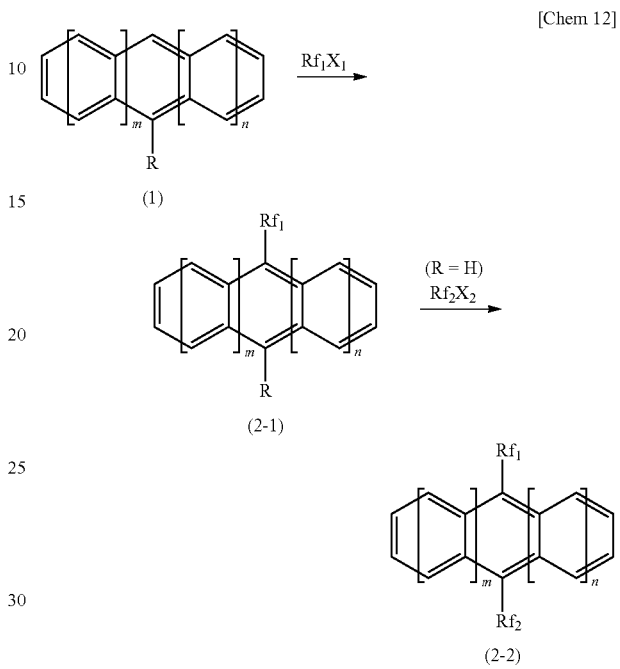

[Chem 12]

The definitions and preferable embodiments of $Rf_1$, $Rf_2$, R, m, and n are the same as those described in the above explanation of the fluorine-containing aromatic compound.

$X_1$ and $X_2$ are a bromine atom or an iodine atom and, in view of good yields, an iodine atom is preferred. $X_1$ and $X_2$ may be the same or different.

Method (a): A fluorine-containing aromatic compound (2-1) is obtained by a manufacturing method including a step of reacting an acene compound (1) with a compound represented by the formula $Rf_1X_1$ in a halogen-containing solvent in the presence of a thiosulfate salt under light irradiation and a step of heating.

Method (b): A compound (2-2) is obtained by a manufacturing method including a step of using the compound (2-1) obtained by the manufacturing method of the method (a) when R is a hydrogen atom in the acene compound (1) and further reacting the compound (2-1) with a compound represented by the formula $Rf_2X_2$ in a halogen-containing solvent in the presence of a thiosulfate salt under light irradiation, and a step of heating.

A compound in which a fluorine-containing alkyl group is mono-substituted is obtained by the method (a) and a di-substituted compound is obtained by the method (b) in which a similar step is repeated. In the method (b), the compound (2-2) in which the structures of $Rf_1$ and $Rf_2$ are different can be synthesized by changing $Rf_2$ of the compound represented by the formula $Rf_2X_2$ from the $Rf_1$ part of the compound represented by the formula $Rf_1X_1$ used in the method (a).

Heating temperature in the method (a) and the method (b) is preferably 200° C. or higher, and particularly preferably from 200 to 300° C.

In the case where R in the acene compound is a hydrogen atom, the following reaction via a compound (1-1') proceeds.

[Chem 13]

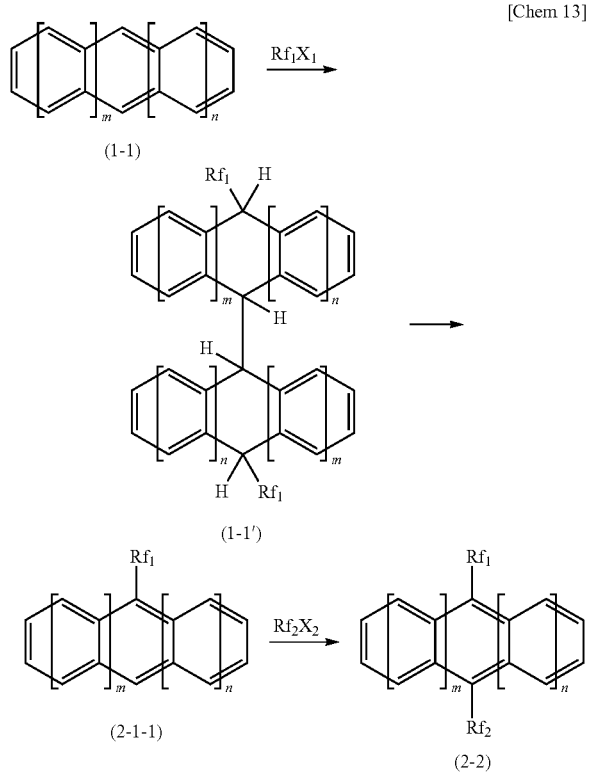

The compound (1-1') is obtained as an intermediate compound by reacting the acene compound (1-1) with the compound represented by the formula $Rf_1X_1$ under light irradiation. Then, a compound (2-1-1) is obtained by heating the compound (1-1'). The fluorine-containing aromatic compound (2-2) is obtained by further reacting the compound (2-1-1) with the compound represented by the formula $Rf_2X_2$.

A film of the fluorine-containing aromatic compound of the present invention can be formed on a substrate by applying the compound (1-1') directly on the substrate and subjecting it to a heat treatment by the method to be mentioned later.

As the acene compound (1) that is a starting material, a known compound can be used. Examples of the compound where R is a hydrogen atom include anthracene, pentacene, and the like. Examples of the compound where R is other than a hydrogen atom include 9-ethylanthracene, 9-propylanthracene, 9-butylanthracene, 9-pentylanthracene, 9-hexylanthracene, 9-heptylanthracene, 9-octylanthracene, 9-decylanthracene, 9-dodecylanthracene, 9-phenylanthracene, 6-ethylpentacene, 6-propylpentacene, 6-butylpentacene, 6-pentylpentacene, 6-hexylpentacene, 6-heptylpentacene, 6-octylpentacene, 6-decylpentacene, 6-dodecylpentacene, 6-phenylpentacene, and the like.

The halogen-containing solvent to be used in the manufacture is preferably a halogenated aliphatic solvent. The halogen atom in the halogen-containing solvent is preferably a chlorine atom or a fluorine atom.

As the halogen-containing solvent, there may be exemplified chlorinated hydrocarbons, chlorinated fluorinated hydrocarbons, and fluorine-containing ether compounds. Specifically, there can be used methylene chloride, chloroform, 2,3,3-trichloroheptafluorobutane, 1,1,1,3-tetrachlorotetrafluoropropane, 1,1,1-trichloropentafluoropropane, 1,1-dichloro-2,2,3,3,3-pentafluoropropane, 1,3-dichloro-1,2,2,3,3-pentafluoropropane, carbon tetrachloride, 1,2-dichloroethane, $n-C_6F_{13}-C_2H_5$, $n-C_4F_9OCH_3$, $n-C_4F_9OC_2H_5$, and the like. Of these, chlorinated hydrocarbons such as methylene chloride; chlorinated fluorinated hydrocarbons such as 1,1-dichloro-2,2,3,3,3-pentafluoropropane and 1,3-dichloro-1,2,2,3,3-pentafluoropropane are preferred, and methylene chloride is particularly preferred.

$Rf_1X_1$ and $Rf_2X_2$ are an iodide or bromide of a fluorine-containing alkane and are preferably a perfluoroalkyl iodide or a perfluoroalkyl bromide, and particularly preferably a perfluoroalkyl iodide.

The salt in the thiosulfate salt is not particularly limited. As the thiosulfate salt, sodium thiosulfate and ammonium thiosulfate are more preferred and sodium thiosulfate is particularly preferred. Moreover, the use amount is from 5 to 50 mol relative to the acene compound (1 g) or is preferably from 2 to 20 mol relative to the total amount of $Rf_1X_1$ and $Rf_2X_2$, and usually, is preferably an amount on the basis of the total amount of $Rf_1X_1$ and $Rf_2X_2$.

Reaction temperature in the present reaction is preferably from 0 to 60° C., and more preferably from 10 to 30° C.

In the light irradiation reaction of the present invention, it is preferred to use ultraviolet rays. As a ultraviolet ray source, those capable of radiating ultraviolet rays of 250 to 600 nm, which are usually used for chemical reactions, decomposition, sterilization, and the like, are preferred, and a high-pressure mercury lamp is preferred. The wavelength for ultraviolet irradiation is preferably from 300 to 600 nm, and particularly preferably 330 to 470 nm. Moreover, the ultraviolet irradiation reaction to be used in the present invention can be performed by a known light irradiation apparatus. Specifically, a merry-go-round type photoreaction apparatus and the like may be mentioned.

Light irradiation time is preferably from 1 to 24 hours, particularly preferably from 1 to 8 hours.

According to the above methods (a) and (b), since a heavy metal coupling reaction is not used in the introduction of the fluorine-containing alkyl group, no heavy metal is contained in the product or, if contained, the ratio thereof can be made very small. With regard to the content of metals contained in the product obtained by the manufacturing method of the present invention, the metal content of each of Ni, Cu, Zn, and Pd is 1 ppm by mass or less and the total content of the metals can be made 10 ppm by mass or less based on 1 g of the compound.

<Organic Semiconductor Material>

The organic semiconductor material of the present invention means a material which contains the fluorine-containing aromatic compound having a specific structure and is to be used as an organic semiconductor. The organic semiconductor material of the present invention may be composed of the fluorine-containing aromatic compound of the present invention alone or may contain other components. As the other components, for example, other organic semiconductor materials and various dopants may be mentioned. As the dopant, for example, in the case of being used as a light-emitting layer of an organic EL element, coumarin, quinacridone, rubrene, stilbene-based derivatives, fluorescent dyes, and the like can be used.

The fluorine-containing aromatic compound of the present invention has a melting point of lower than about 300° C. This is considered to be attributable to the fact that, thermal movement owing to the chain length of the fluorine-containing alkyl group weakens the crystallinity between the molecules.

Moreover, it is considered that the presence of the fluorine-containing alkyl group stabilizes a molecular arrangement (π-π stacking) where the planes of the aromatic rings as a main skeleton face each other, and thus contributes to the realization of the charge mobility.

Moreover, since the fluorine-containing alkyl group is located at least one of 9- and 10-positions in the case where the fluorine-containing aromatic compound is anthracene and at least one of 6- and 13-positions in the case of pentacene, dimerization of the pentacene compounds themselves is prevented and deterioration behavior of a quinone skeleton, which may be caused by oxygen or moisture in the air, is also prevented.

Furthermore, fluorine-containing alkyl groups of adjacent molecules are aggregated by affinity therebetween (a fluorophilic effect), so that the groups contribute to more efficient charge transfer. Therefore, when the fluorine-containing aromatic compound of the present invention is used, the preparation of an organic semiconductor thin film maintaining high carrier mobility and an electronic element utilizing the same, such as a transistor, can be realized.

While anthracene and pentacene act as p-type semiconductors, the fluorine-containing aromatic compound of the present invention has conductivity and electronic transition energy changing depending on the substituent. Accordingly, when the fluorine-containing aromatic compound of the present invention is used, an organic semiconductor material which conductive type is controlled can be obtained.

<Organic Semiconductor Thin Film>

The organic semiconductor material according to the present invention can form an organic semiconductor film on a substrate according to a usual manufacturing method using a dry process or a wet process. As the film, a thin film, a thick film, or a film having crystallinity may be mentioned.

In the case of forming a thin film by a dry process, there may be used a known method such as a vacuum deposition method, an MBE (Molecular Beam Epitaxy) method, a sputtering method, a laser deposition method, or a vapor-phase transport growth method.

The obtained organic semiconductor thin film functions as charge transport members of various functional elements such as a photoelectric conversion element, a thin-film transistor element, and a light-emitting element, and thus it is possible to apply to a variety of electronic devices.

In the case where the thin film is formed by using the vacuum deposition method, the MBE method, or the vapor-phase transport growth method, the organic semiconductor material is heated and sublimed vapor is transported to the substrate surface under high vacuum, vacuum, low vacuum, or normal pressure. The formation of the thin film can be carried out according to known methods or conditions. Specifically, substrate temperature is preferably from 20 to 200° C. and a thin-film growth rate is preferably from 0.001 to 1,000 nm/sec. Under such conditions, a film having crystallinity and having surface smoothness of the thin film can be formed.

When the substrate temperature is a low temperature, the thin film is prone to be amorphous, while when the temperature is a high temperature, the surface smoothness of the thin film tends to decrease. Further, when the thin-film growth rate is low, the crystallinity is prone to decrease, while when the rate is too high, the surface smoothness of the thin film tends to decrease.

In the case of forming the thin film by a wet process, the organic semiconductor thin film can be formed by covering a substrate with a solution obtained by dissolving the organic semiconductor material containing the fluorine-containing aromatic compound in an organic solvent.

Since the fluorine-containing aromatic compound of the present invention is a compound having an improved solubility in organic solvents as compared with conventional organic semiconductor materials, a wet process is applicable. The film formation by a wet process has the advantage of being able to process without damaging semiconductor crystals.

As film formation methods in a wet process (methods for covering a substrate), coating, spraying, and contact, and the like may be mentioned. Specifically, there may be mentioned known methods such as a spin coating method, a casting method, a dip coating method, an ink-jet method, a doctor blade method, a screen printing method, and a dispense method. Moreover, in the case of a plate-like crystal or a thick-film state, the casting method or the like can be adopted. As the film formation method and the organic solvent, it is preferable to select a suitable combination for the device to be prepared.

In the wet process, a method of controlling crystal growth by providing at least one selected from temperature gradient, electric field, and magnetic field to the interface between the solution of the fluorine-containing aromatic compound and the substrate can be adopted. When such a method is adopted, an organic semiconductor thin film having a higher crystallinity can be manufactured and excellent semiconductor properties based on the performance of the thin film having a high crystallinity can be obtained. Moreover, also by adopting a solvent atmosphere as the environmental atmosphere at the time of the wet-process film formation, an organic semiconductor thin film having a high crystallinity can be manufactured with controlling the vapor pressure in solvent drying.

In the wet process, as examples of the organic solvent in which the fluorine-containing aromatic compound can be dissolved, there may be mentioned examples of non-halogen solvents, for example, aliphatic hydrocarbons such as pentane, hexane, and heptane; alicyclic hydrocarbons such as cyclohexane; aromatic hydrocarbons such as benzene, toluene, xylene, phenol, and cresol; ethers such as diethyl ether, tert-butyl methyl ether, tetrahydrofuran, and dioxane; alcohols such as methanol, ethanol, and 2-propanol; mixtures thereof; and the like.

As examples of halogen-containing solvents, there may be exemplified chlorinated hydrocarbons, chlorinated aromatic hydrocarbons, fluorinated hydrocarbons, chlorinated fluorinated hydrocarbons, and fluorine-containing ether compounds. Specifically, there may be mentioned methylene chloride, chloroform, 1,2-dichloroethane, chlorobenzene, 1,2-dichlorobenzene, 1,2,4-trichlorobenzene, 2,3,3-trichloroheptafluorobutane, 1,1,1,3-tetrachloro-2,2,3,3-tetrafluoropropane, 1,1,1-trichloropentafluoropropane, 1,1-dichloro-2,2,3,3,3-pentafluoropropane, 1,3-dichloro-1,1,2,2,3-pentafluoropropane, carbon tetrachloride, 1,2-dichloroethane, dichloropentafluoropropane, n-$C_6F_{13}$—$C_2H_5$, n-$C_4F_9OCH_3$, n-$C_4F_9OC_2H_5$, and the like.

Only one kind of the solvent may be used or two or more kinds thereof may be used in combination. In the case of using two or more kinds thereof in combination, it is preferred to use a non-halogen solvent and a halogen-containing solvent in combination, and a solvent obtained by mixing them in an arbitrary ratio is preferred.

In the case of performing the wet process with dissolving the fluorine-containing aromatic compound of the present invention in an organic solvent, from the standpoints of work efficiency and the like, the concentration of the organic semiconductor material to be dissolved in the organic solvent is preferably 0.01% by weight or more, particularly preferably from 0.01 to 10% by weight and especially preferably from 0.2 to 10% by weight in the organic solvent. Since the fluorine-containing aromatic compound of the present invention is excellent in solubility in organic solvents, it is also suitable to use the compound after the fluorine-containing aromatic compound obtained by the above manufacturing method is made highly pure by a simple and easy purification method such as column chromatography or recrystallization.

The covering of the substrate by the wet process can be performed under the atmospheric air or under an inert gas atmosphere. Particularly, in the case where the solution of the semiconductor material is easily oxidized, the covering is preferably performed under an inert gas atmosphere, and nitrogen, argon, or the like can be used.

After the substrate is covered, by evaporating the solvent, an organic semiconductor thin film is formed. When an amount of the remaining solvent in the thin film is large, there is a concern that stability and semiconductor properties of the thin film decrease. Therefore, it is preferable to remove the remaining solvent by performing a heat treatment or a pressure-reducing treatment again after the thin film formation.

The shape of the substrate usable in the wet process is not particularly limited and usually, a sheet-like substrate or a plate-like substrate is preferred. The material to be used as the substrate is also not particularly limited, and ceramics, metal substrates, semiconductors, resins, paper, nonwoven fabrics, and the like may be mentioned.

As examples of the substrate, there may be mentioned substrates of glass, quartz, aluminum oxide, sapphire, silicon nitride, silicon carbide, and the like. As the metal substrate, substrates of gold, copper, silver, and the like may be mentioned. As the semiconductor substrate, there may be mentioned substrates of silicon (crystalline silicon, amorphous silicon), germanium, gallium arsenide, gallium phosphide, gallium nitride, and the like. As the resin substrate, there may be mentioned substrates of polyester, polyethylene, polypropylene, polyvinyl, polyvinyl alcohol, ethylene-vinyl alcohol copolymer, cyclic polyolefin, polyimide, polyamide, polystyrene, polycarbonate, polyether sulfone, polysulfone, polymethyl methacrylate, polyethylene terephthalate, triacetylcellulose, norbornene, and the like.

By using the fluorine-containing aromatic compound, the resulting organic semiconductor thin film can be made a crystalline thin film. A crystalline thin film has high carrier mobility owing to the high crystallinity and thereby excellent organic semiconductor device properties are realized.

A crystalline state of the thin film can be known by grazing incidence X-ray diffraction measurement of the thin film, transmission electron beam diffraction, or a method of allowing X-ray to enter into an edge part of the thin film to measure diffraction. Particularly, it is preferred to use the grazing incidence X-ray diffraction that is a crystal analysis method in the thin film field.

As the X-ray diffraction method, there are an Out-of-plane XRD method and an In-plane XRD method depending on the direction of a lattice plane to be measured. The Out-of-plane XRD method is a method of observing a lattice plane parallel to the substrate. The In-plane XRD method is a method of observing a lattice plane perpendicular to the substrate.

The fact that a thin film has crystallinity means that diffraction peak(s) derived from the organic semiconductor material forming the thin film are observed. Specifically, it means that there are observed diffraction based on a crystal lattice of the organic semiconductor material, diffraction derived from molecular length, or characteristic diffraction peak(s) appearing at the time when molecules have an orientation of arranging parallel or perpendicular to the substrate. In the case where a thin film is in a non-crystalline state, the diffraction is not observed. A thin film appearing diffraction peak(s) means that the film is a crystalline thin film.

Thickness of the organic semiconductor thin film layer for use in an organic semiconductor element is usually preferably from 10 to 1,000 nm.

<Organic Semiconductor Element, Organic Semiconductor Transistor>

The fluorine-containing aromatic compound of the present invention has high carrier mobility. Accordingly, an organic semiconductor material containing the same can form an organic semiconductor thin film without impairing the high carrier mobility of the fluorine-containing aromatic compound.

An organic semiconductor element containing a semiconductor layer formed by stacking layers of the organic semiconductor thin film is very useful for various semiconductor devices.

Examples of the semiconductor devices include organic semiconductor transistors, organic semiconductor lasers, organic photoelectric conversion devices, organic molecular memories, and the like. Of these, as the semiconductor device, an organic semiconductor transistor is preferred and further, a field effect transistor (FET) is more preferred.

The organic semiconductor transistor is usually composed of a substrate, a gate electrode, an insulator layer (dielectric layer), a source electrode, a drain electrode, and a semiconductor layer. Besides, a back gate, a bulk, and the like may be included.

The order and the like of disposing the constituent elements in the organic semiconductor transistor are not particularly limited. Moreover, of the above constituent elements, the gate electrode, source electrode, drain electrode, and semiconductor layer may be provided as those each composed of plural layers. In the case where plural layers of semiconductor layer are present, the layers may be provided in the same plane or may be provided by stacking them.

The fluorine-containing aromatic compound of the present invention has high carrier mobility and has excellent properties as a semiconductor material. Since the fluorine-containing aromatic compound of the present invention has a high solubility in organic solvents, a simple and convenient film formation process such as a casting method or a printing method can be utilized, so that the organic semiconductor thin film or the organic semiconductor element can be manufactured without impairing the high carrier mobility of the fluorine-containing aromatic compound.

The compound (1-1') of the present invention can be utilized as a conversion-type precursor material of a coating-type organic semiconductor material. Specifically, when a solution obtained by dissolving the compound (1-1') in an organic solvent is applied on a substrate and then a thermal treatment at 220° C. or higher is conducted under vacuum, it can be converted into the fluorine-containing aromatic compound (2-1-1) of the present invention. By this method, an organic semiconductor thin film or organic semiconductor element of the fluorine-containing aromatic compound can be manufactured.

EXAMPLES

The following will specifically describe the present invention with reference to Examples but the present invention should not be construed as being limited to these Examples.

For nuclear magnetic resonance analysis in the present Examples, a Fourier transform high resolution nuclear magnetic resonance apparatus (NMR), JNM-AL400 manufactured by JEOL Ltd. was used. Multiplicity is abbreviated as follows: singlet: s, doublet: d, triplet: t, quartet: q, multiplet: m, broad: br.

$^1$H-NMR (400 MHz) was measured by using chloroform-d (CDCl$_3$) as a solvent and tetramethylsilane (TMS) as an internal standard.

$^{13}$C-NMR (100 MHz) was measured by using chloroform-d (CDCl$_3$) as a solvent and chloroform-d (CDCl$_3$) as an internal standard.

$^{19}$F-NMR (313 MHz) was measured by using chloroform-d (CDCl$_3$) as a solvent and hexafluorobenzene (C$_6$F$_6$) as an internal standard, with regarding C$_6$F$_6$ as −163 ppm, and CFCl$_3$ as 0 ppm.

For mass spectroscopy, Extractive manufactured by Thermo Fischer KK or JMF-S3000 SpiralTOF (MALDI-TOFMS) manufactured by JEOL Ltd. was used. For Extractive, a sample was dissolved in methanol and, with regard to the ionization method, measurement was performed by using ESI or APCI. For MALDI-TOFMS, a sample was dissolved in tetrahydrofuran in 0.2% by mass and analysis was performed while mixing with a cationization agent. As the cationization agent, a 0.1% by mass sodium iodide/acetonitrile solution was used.

For melting point measurement, a differential scanning calorimeter TG-DTA manufactured by Bruker was used.

Example 1-a

Synthetic Example of 9-Perfluorohexylanthracene (Compound (a))

Anthracene (manufactured by Tokyo Chemical Industry Co., Ltd., 0.1782 g, 1.0 mmol) was dissolved in methylene chloride (manufactured by Kanto Chemical Co., Inc., 25 mL) in a Pyrex tube. Then, n-C$_6$F$_{13}$I (manufactured by Daikin Industries, Ltd., 0.24 mL, 1.1 mmol), sodium thiosulfate (manufactured by Kanto Chemical Co., Inc., 1.5811 g, 10 mmol) and water (5 mL) were added thereto and, while the temperature of the reaction system was kept constant with letting cooling water flow, ultraviolet irradiation was conducted by using a 450 W high-pressure mercury lamp (manufactured by Ultraviolet Company, an ultraviolet lamp UVG-11). With regard to the proceeding of the reaction, using thin-layer chromatography, (TLC: manufactured by Merck Corporation, silica gel 60F254), disappearance of anthracene and appearance of a product were appropriately confirmed. After irradiation for 6 hours, an aqueous layer was removed and, after the reaction solution was extracted with methylene chloride, the obtained organic layer was dried over anhydrous sodium sulfate and filtrated. The filtrate was subjected to solvent removal on a rotary evaporator and concentrated, and the obtained mixture was heated at 220° C. for 1 hour. Thereafter, separation and purification were performed by using column chromatography (manufactured by Kanto Chemical Co., Inc., silica gel 60FC (spherical)) (developing solvent: hexane (manufactured by Godo Co., Ltd.)) to obtain 9-perfluorohexylanthracene (Compound (a)) (0.4365 g, 88% yield) that is the objective compound as a yellow solid.

[Chem 14]

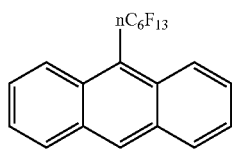

(a)

(Analytical Results)

$^1$H NMR (400 MHz, TMS, CDCl$_3$) δ 8.68 (1H, s, Ar—H), 8.40 (2H, d, J=9.2 Hz, Ar—H), 8.05 (2H, d, J=8.4 Hz, Ar—H), 7.61-7.57 (2H, m, Ar—H), 7.53-7.49 (2H, m, Ar—H).

$^{13}$C NMR (100 MHz, CDCl$_3$) δ 134.46 (s), 131.52 (s), 131.33 (s), 129.38 (s), 127.87 (s), 125.39-125.23 (m), 125.07 (s).

$^{19}$F NMR (400 MHz, CDCl$_3$) δ −80.6 (3F, s, CF$_3$), −93.4 (2F, s, CF$_2$), −118.9 (2F, s, CF$_2$), −121.4 (2H, s, CF$_2$), −122.4 (2F, s, CF$_2$), −125.9 (2F, s, CF$_2$)

m.p. (98.7° C.)

HRMS (APCI) m/z 497.05579 ([C$_{20}$H$_9$F$_{13}$+H]$^+$)

Example 1-b

Synthetic Example of 10,10'-Bis(perfluorohexyl)-9, 9',10,10'-tetrahydro-9,9'-bianthracene (Compound (b))

Anthracene (0.1782 g, 1.0 mmol) was dissolved in methylene chloride (25 mL) in a Pyrex tube. Then, n-C$_6$F$_{13}$I (0.24 mL, 1.1 mmol), sodium thiosulfate (1.5811 g, 10 mmol) and water (5 mL) were added thereto and, while the temperature of the reaction system was kept constant with letting cooling water flow, ultraviolet irradiation was conducted by using a 450 W high-pressure mercury lamp (manufactured by Ultraviolet Company, an ultraviolet lamp UVG-11). After irradiation for 6 hours, an aqueous layer was removed and, after the reaction solution was extracted with methylene chloride, the obtained organic layer was dried over anhydrous sodium sulfate and filtrated. After filtration, the filtrate was subjected to solvent removal on a rotary evaporator and concentrated. Thereafter, separation and purification were performed by using column chromatography (manufactured by Kanto Chemical Co., Inc., silica gel 60FC (spherical)) (developing solvent: hexane) to obtain 10,10'-bis(perfluorohexyl)-9,9',10, 10'-tetrahydro-9,9'-bianthracene (Compound (b)) (0.2584 g, 52% yield) as a yellow solid.

[Chem 15]

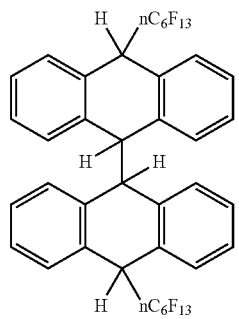

(b)

(Analytical Results)

$^1$H-NMR (400 MHz, TMS, CDCl$_3$) δ 7.57-7.55 (1H, m, Ar—H), 7.52-7.44 (2H, m, Ar—H), 7.37-7.31 (2H, m, Ar—H) 7.15 (1H, t, J=7.2 Hz), 6.75 (1H, t, J=7.2 Hz), 6.24 (1H, d, J=7.6 Hz), 5.61 (1H, s), 5.03 (1H, t, J=18.0 Hz)

$^{13}$C NMR (100 MHz, CDCl$_3$) δ 141.20 (s), 137.63 (s), 130.93 (s), 130.86 (s), 130.62 (s), 130.48 (s), 129.83 (s), 128.72 (s), 126.66 (s), 126.35 (s), 125.93 (s), 125.58 (s), 50.29 (t, J=21.9 Hz) 39.14 (s)

$^{19}$F NMR (400 MHz, CDCl$_3$) δ −80.7 (3F, s, CF$_3$), −110.17 (2F, q, J=270.4 Hz), −118.37 (2F, s, CF$_2$), −121.45 (2F, s, CF$_2$), −122.65 (2F, s, CF$_2$)−125.99 (2F, s, CF$_2$)

m.p. (119.5° C.) (MALDI-TOFMS)

m/z 413 ([C$_{20}$H$_{10}$F$_{13}$]$^+$), 1017 ([C$_{40}$H$_{20}$F$_{26}$+Na]$^+$)

Example 1-c

Synthetic Example of 9-Perfluorohexylanthracene (Compound (a)) Using Compound (b) as Starting Material In a 200 mL eggplant-shaped flask was heated 10,10'-bis(perfluorohexyl)-9,9',10,10'-tetrahydro-9,9'-bianthracene (Compound (b)) (0.2584 g, 0.3 mmol) obtained in Example 1-b at 220° C. for 1 hour. Thereafter, separation and purification were performed by using column chromatography (manufactured by Kanto Chemical Co., Inc., silica gel 60FC (spherical)) (developing solvent: hexane) to obtain a yellow solid. Upon structure determination using the above-described analytical methods, it was confirmed that the solid was 9-perfluorohexylanthracene (Compound (a)).

Example 2

Synthetic Example of 9-Perfluoro-n-butylanthracene (Compound (c))

A 9-perfluoro-n-butylanthracene (Compound (c)) (0.3357 g, 85% yield) was obtained as a yellow solid in the same manner as in Example 1-a except that C$_6$F$_{13}$I was changed to C$_4$F$_9$I (manufactured by Daikin Industries, Ltd., 0.22 mL, 1.1 mL).

[Chem 16]

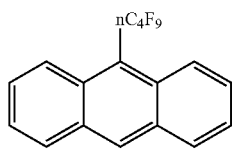

(c)

(Analytical Results)

$^1$H NMR (400 MHz, TMS, CDCl$_3$) δ 8.68 (1H, s, Ar—H), 8.40 (2H, d, J=9.2 Hz, Ar—H), 8.04 (2H, d, J=8.4 Hz, Ar—H), 7.60-7.57 (2H, m, Ar—H), 7.53-7.49 (2H, m, Ar—H)

$^{13}$C NMR (100 MHz, CDCl$_3$) δ 134.43 (s), 131.52 (s), 131.30 (s), 129.35 (s), 127.83 (s), 125.39-125.23 (m), 125.05 (s)

$^{19}$F NMR (400 MHz, CDCl$_3$) δ −80.7 (3F, s, CF$_3$), −93.5 (2F, s, CF$_2$), −119.9 (2F, s, CF$_2$), −125.3 (2F, s, CF$_2$)

m.p. (76.6° C.)

HRMS (APCI) m/z 497.05579 ([C$_{20}$H$_9$F$_{13}$+H]$^+$)

Example 3

Synthetic Example of 9,10-Bis(perfluorobutyl)anthracene (Compound (d))

The compound (c) (0.3951 g, 1.0 mmol) was dissolved in methylene chloride (23 mL) in a Pyrex tube. Then, n-C$_4$F$_9$I (0.22 mL, 1.1 mmol), sodium thiosulfate (1.5811 g, 10 mmol) and water (5 mL) were added thereto and, while the temperature of the reaction system was kept constant with letting cooling water flow, ultraviolet irradiation was conducted by using a 450 W high-pressure mercury lamp (manufactured by Ultraviolet Company, an ultraviolet lamp UVG-11). After irradiation for 6 hours, an aqueous layer was removed and, after the reaction solution was extracted with methylene chloride, the obtained organic layer was dried over anhydrous sodium sulfate and filtrated. The filtrate was subjected to solvent removal on a rotary evaporator and concentrated. The obtained mixture was dissolved in ethyl acetate (manufactured by Godo Co., Ltd.) and a precipitate was removed by filtration. A concentrated filtrate was separated and purified by using column chromatography (manufactured by Kanto Chemical Co., Inc., silica gel 60FC (spherical)) (developing solvent: hexane) to obtain 9,10-bis(perfluorobutyl)anthracene (Compound (d)) (0.1317 g, 21% yield) as a yellow solid.

[Chem 17]

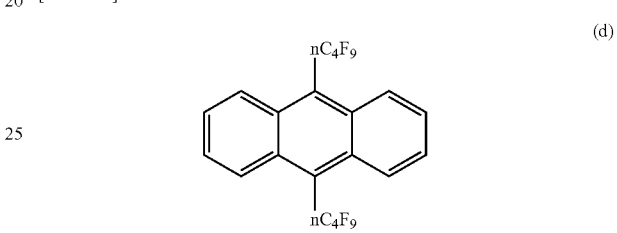

(d)

(Analytical Results)

$^1$H NMR (400 MHz, TMS, CDCl$_3$) δ 8.43-8.38 (4H, m, Ar—H), 7.62-7.59 (4H, m, Ar—H)

$^{13}$C NMR (100 MHz, CDCl$_3$) δ 131.13 (s), 126.93 (s), 125.98-124.23 (m)

$^{19}$F NMR (400 MHz, CDCl$_3$) δ −80.6 (3F, s, CF$_3$), −91.1 (2F, s, CF$_2$), −117.8 (2F, s, CF$_2$), −125.5 (2F, s, CF$_2$)

m.p. (119.4° C.)

HRMS (APCI) m/z 614.03418 ([C$_{22}$H$_9$F$_{18}$]$^+$)

Example 4

Synthetic Example of 9,10-Bis(perfluorohexyl)anthracene (Compound (e))

The compound (a) (0.4365 g, 0.9 mmol) was dissolved in methylene chloride (23 mL) in a Pyrex tube. Then, n-C$_6$F$_{13}$I (0.22 mL, 1.0 mmol), sodium thiosulfate (1.423 g, 9.0 mmol) and water (5 mL) were added thereto and, while the temperature of the reaction system was kept constant with letting cooling water flow, ultraviolet irradiation was conducted by using a 450 W high-pressure mercury lamp (manufactured by Ultraviolet Company, an ultraviolet lamp UVG-11). After irradiation for 6 hours, an aqueous layer was removed and, after the reaction solution was extracted with methylene chloride, the obtained organic layer was dried over anhydrous sodium sulfate and filtrated. The filtrate was subjected to solvent removal on a rotary evaporator and concentrated. The obtained mixture was dissolved in ethyl acetate and a precipitate was removed by filtration. A concentrated filtrate was separated and purified by using column chromatography (manufactured by Kanto Chemical Co., Inc., silica gel 60FC (spherical)) (developing solvent: hexane) and then purification by sublimation was performed. An objective product, 9,10-bis(perfluorohexyl)anthracene (Compound (e)) (0.1092 g, 15% yield) was obtained as a yellow solid.

[Chem 18]

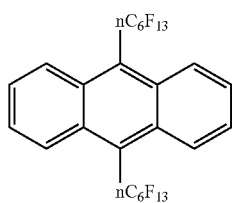

(e)

(Analytical Results)

$^1$H NMR (400 MHz, TMS, CDCl$_3$) δ 8.45-8.40 (4H, m, Ar—H), 7.63-7.59 (4H, m, Ar—H)

$^{13}$C NMR (100 MHz, CDCl$_3$) δ 131.09 (s), 126.93 (s), 125.54-125.43 (m)

$^{19}$F NMR (400 MHz, CDCl$_3$) δ −80.5 (3F, s, CF$_3$), −90.8 (2F, s, CF$_2$), −116.8 (2F, s, CF$_2$), −121.4 (2F, s, CF$_2$), −122.4 (2F, s, CF$_2$), −125.8 (2F, s, CF$_2$)

m.p. (147.4° C.)

HRMS (APCI) m/z 814.01935 ([C$_{26}$H$_8$F$_{26}$]$^+$)

Example 5

Synthetic Example of 9-Perfluoro-isopropylanthracene (Compound (f))

Anthracene (0.1782 g, 1.0 mmol) was dissolved in methylene chloride (25 mL) in a Pyrex tube. Then, CF(CF$_3$)$_2$I ((manufactured by Daikin Industries, Ltd., mL, 1.5 mmol), sodium thiosulfate (1.5811 g, 10 mmol) and water (5 mL) were added thereto and, while the temperature of the reaction system was kept constant with letting cooling water flow, ultraviolet irradiation was conducted by using a 450 W high-pressure mercury lamp (manufactured by Ultraviolet Company, an ultraviolet lamp UVG-11). After irradiation for 6 hours, an aqueous layer was removed and, after the reaction solution was extracted with methylene chloride, the obtained organic layer was dried over anhydrous sodium sulfate and filtrated. The filtrate was subjected to solvent removal on a rotary evaporator and concentrated. The obtained mixture was heated at 220° C. for 1 hour. Thereafter, separation and purification were performed by using column chromatography (manufactured by Kanto Chemical Co., Inc., silica gel 60FC (spherical)) (developing solvent: hexane (manufactured by Godo Co., Ltd.)) to obtain 9-perfluoro-isopropylanthracene (Compound (f)) (0.2056 g, 46% yield) that is the objective compound as a yellow solid.

$^1$H NMR (400 MHz, TMS, CDCl$_3$) δ 8.63 (1H, s, Ar—H), 8.55 (1H, t, J=8.4 Hz, Ar—H), 8.28 (1H, d, J=9.2 Hz, Ar—H), 8.04 (2H, t, J=6.8 Hz, Ar—H) 7.58-7.47 (4H, m, Ar—H)

$^{19}$F NMR (400 MHz, CDCl$_3$) δ −69.9 (6F, s, CF$_3$), −73.6 (1F, s, CF)

[Chem 19]

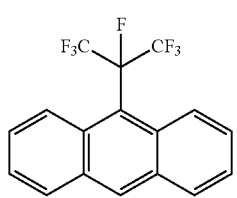

(f)

Example 6

Synthetic Example of 9-Perfluorobutyl-10-perfluorohexylanthracene (Compound (g))

A 9-perfluorobutyl-10-perfluorohexylanthracene (Compound (g)) (0.1092 g, 15% yield) was obtained as a yellow solid in the same manner as in Example 4 except that C$_6$F$_{13}$I was changed to C$_4$F$_9$I.

[Chem 20]

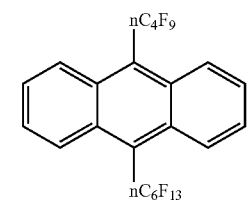

(g)

(Analytical Results)

$^1$H NMR (400 MHz, TMS, CDCl$_3$) δ 8.45-8.40 (4H, m, Ar—H), 7.63-7.59 (4H, m, Ar—H)

$^{13}$C NMR (100 MHz, CDCl$_3$) δ 131.07 (s), 126.92 (s), 125.56-125.43 (m)

$^{19}$F NMR (400 MHz, CDCl$_3$) δ −80.5 (6F, s, CF$_3$), −90.2 (4F, d, J=61.2 Hz, CF$_2$), −116.8 (2F, s, CF$_2$), −117.8 (2F, s, CF$_2$), −121.4 (2F, s, CF$_2$), −122.4 (2F, s, CF$_2$), −125.5 (2F, s, CF$_2$), −125.8 (2F, s, CF$_2$), m.p. (114.9° C.)

HRMS (APCI) m/z 714.02759 ([C$_{24}$H$_8$F$_{22}$]$^+$)

Example 7-a

Synthetic Example of 13-Perfluorohexylpentacene (Compound h))

A 13-perfluorohexylpentacene (Compound (h)) was obtained as a dark blue solid in the same manner as in Example 1-a except that anthracene was changed to pentacene.

[Chem 21]

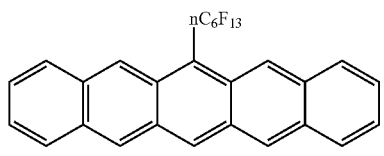

(h)

(Analytical Results)

$^1$H NMR (400 MHz, TMS, CDCl$_3$) δ 8.45-8.40 (4H, m, Ar—H), 7.63-7.59 (4H, m, Ar—H)

$^{19}$F NMR (400 MHz, CDCl$_3$) δ −80.5 (3F, s, CF$_3$), −90.8 (2F, s, CF$_2$), −116.8 (2F, s, CF$_2$), −121.4 (2F, s, CF$_2$), −122.4 (2F, s, CF$_2$), −125.8 (2F, s, CF$_2$)

Example 7-b

Synthetic Example of 6,13-Bis(perfluorohexyl)pentacene (Compound (i)) from Compound (h)

The objective product (i) can be obtained as a dark blue solid in the same manner as in Example 4 except that the compound (a) is changed to the compound (h).

HRMS (APCI) m/z 914. ([C$_{34}$H$_{12}$F$_{26}$]$^+$)

[Chem 22]

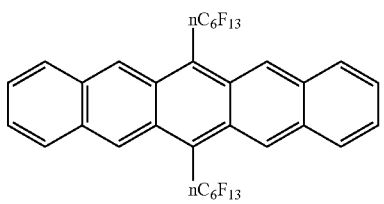

(i)

Example 8

An objective product 9-perfluorohexylanthracene (Compound (a)) was obtained as a yellow solid in the same manner as in Example 1-a except that methylene chloride was changed to AK225 (manufactured by Asahi Glass Co., Ltd., a fluorine-based solvent, 25 mL).

Example 9

Trifluoromethylnaphthalene (0.1472 g, 66% yield, α:β=85:15) was obtained in the same manner as in Example 1-a except that anthracene was changed to naphthalene (manufactured by Kanto Chemical Co., Inc., 0.0667 g, 0.5 mmol) and ultraviolet irradiation was conducted for 22 hours. The isomer ratio was determined based on a peak area ratio corresponding to Ar—H on $^1$H NMR.

(Analytical Results)

$^1$H NMR (400 MHz, TMS, CDCl$_3$) δ 8.29 (1H, d, J=9.2 Hz, Ar—H), 7.63-7.40 (4H, m, Ar—H), 7.63-7.59 (4H, m, Ar—H)

$^{19}$F NMR (400 MHz, CDCl$_3$) δ −80.9 (3F, s, CF$_3$), −104.1 (3F, s, CF$_3$), −109.7 (3F, s, CF$_3$), −120.06 (3F, s, CF$_3$), −121.322 (3F, s, CF$_3$), −122.6 (3F, s, CF$_3$), −126.05 (3F, s, CF$_3$)

MS (ESI) m/z 446

Reference Example 1

Under a nitrogen atmosphere, 9,10-dibromoanthracene (0.6 g, 1.78 mmol) and a copper powder (1.14 g, 17.8 mmol) were added to a 200 mL reaction vessel and were dissolved in anhydrous dimethyl sulfoxide (25 mL). α,α,α-Benzotrifluoride (25 mL) and C$_6$F$_{13}$I (1.96 mL, 8.93 mmol) were added thereto and reaction was carried out at 130° C. for 4 hours. After quenching with ice-water, the reaction solution was extracted with methylene chloride. Thereafter, the obtained organic layer was dried over anhydrous sodium sulfate and then filtrated. The filtrate was subjected to solvent removal on a rotary evaporator and, thereafter, separation and purification were conducted by using column chromatography. A 9,10-bis(perfluorohexyl)anthracene was obtained as a yellow solid.

<Method for Quantitative Determination Test 1 of Metal Content in Compound>

The 9,10-bis(perfluorohexyl)anthracenes obtained in each of Example 4 and Reference Example 1 was subjected to a contamination analysis test of various metal elements after sublimation purification (once).

A sample 5 mg was weighed in a platinum crucible and was converted into ashes by means of a gas burner. Then, 0.2 mL of sulfuric acid was charged thereinto and, after evaporation to dryness on a hot plate, temperature was raised to perform a white smoke treatment. A residue was dissolved with a hydrochloric acid solution and various elements (Li, Na, Mg, Al, K, Ca, Cr, Mn, Fe, Co, Ni, Cu, Zn, Pb, P) were quantitatively determined by ICP-MS method. As an apparatus, quadrupole ICP-MS (ELAN-DRCII manufactured by PerkinElmer Co., Ltd.) was used. For quantitative determination of P, dipole ICP-MS (ELEMENT2 manufactured by Thermo Fisher Scientific K.K.) was used.

Results are shown in Table 1.

TABLE 1

Quantitative Determination Test 1 of Metal Content (μg/g)

| Element | Example 4 | Reference Example 1 | Element | Example 4 | Reference Example 1 |
| --- | --- | --- | --- | --- | --- |
| Li | <1 | <1 | Fe | 1 | 14 |
| Na | 1 | 8 | Co | <1 | <1 |
| Mg | <1 | 4 | Ni | <1 | <1 |
| Al | 1 | <1 | Cu | <1 | 32 |
| K | <1 | 2 | Zn | <1 | <1 |
| Ca | 3 | 21 | Pb | <1 | <1 |
| Cr | <1 | 2 | P | <1 | <1 |
| Mn | <1 | <1 | | | |

<Method for Quantitative Determination Test 2 of Halogen Content in Compound>

The 9,10-bis(perfluorohexyl)anthracenes obtained in each of Example 4 and Reference Example 1 was subjected to a contamination analysis test of Br and Cl elements after sublimation purification (once).

A sample 5 mg was converted into a solution through a pre-treatment by an oxygen combustion flask method, and Br and Cl were quantitatively determined by an ion chromatograph method (an ion chromatography DX500 Model manufactured by Dionex Company). Contents of Br and Cl elements in the sample were shown in Table 2.

TABLE 2

Quantitative Determination Test 2 of Halogen Content (wt %)

| Element | Example 4 | Reference Example 1 |
| --- | --- | --- |
| Br | <0.01 | 1.5 |
| Cl | 0.03 | <0.01 |

From Table 1 and Table 2, it is realized that the fluorine-containing aromatic compounds synthesized by the manufacturing method of the present invention have a very small content of metal impurities. In comparison with the metal content of commercially available organic semiconductors (about 25 ppm by mass), the content of metals proves to be markedly low.

<Solubility Test of Compound>

In order to investigate applicability of the compound (e) obtained in the above Example 4 to a wet process, a solubility test of the compound in various solvents was conducted. In addition, a solubility test of anthracene was also conducted as Reference Example 2.

Specifically, 20 mg of a sample was weighed and it was visually judged whether it dissolves in 10 g of a solvent at room temperature (0.2% by mass).

Results are shown in Table 3.

TABLE 3

| Solvent | Hexane | Cyclohexane | Chloroform | 1,2-Dichlorobenzene |
|---|---|---|---|---|
| Example 4 Compound (e) | Yes | Yes | Yes | Yes |
| Reference Example 2 Anthracene | No | No | Yes | Yes |

In Table 3, "Yes" represents "soluble" and "No" represents "insoluble".

As a result of the solubility test, the compounds synthesized in the present invention are soluble even in low polar solvents such as hexane and cyclohexane.

<Semiconductor Material and Mobility Evaluation>

A cleaned silicon substrate was immersed in a toluene solution of n-octyltrichlorosilane to treat surface of the silicon oxide film. An organic semiconductor layer was formed by vacuum deposition of the compound (e) (9,10-bis(perfluorohexyl)anthracene) obtained in Example 4 onto the substrate (back pressure: up to $10^{-4}$ Pa, deposition rate: 0.1 Å/s, substrate temperature: 25° C., film thickness: 70 nm).

Gold was vacuum deposited on an upper part of the organic semiconductor layer (back pressure: up to $10^{-4}$ Pa, deposition rate: 1 to 2 Å/s, film thickness: 50 nm) by using a shadow mask to form source and drain electrodes (channel length: 50 μm, channel width: 1 mm). The organic semiconductor layer and the silicon oxide film existing at a site different from the electrodes were scraped away, and a conductive paste (DOTITE D-550 manufactured by Fujikura Kasei Co., Ltd.) was attached thereto, and a solvent was dried. Thus, a field effect transistor (FET) element having a top-contact bottom-gate structure was prepared.

Using the part as a gate electrode, voltage was imparted to the silicon substrate. Electrical properties of the obtained FET (field effect transistor) element were evaluated under vacuum (<$5 \times 10^{-3}$ Pa) by using a semiconductor device analyzer B1500A manufactured by Agilent Company. As a result, the element exhibited properties as an n-type transistor element. Field effect mobility was determined from a saturated region in current-voltage properties of the organic thin-film transistor. The carrier mobility was $9.1 \times 10^{-5}$ cm$^2$/V·s.

By the same method, formation of an organic semiconductor layer and formation of an FET element can be performed by using the compound (d) (9,10-bis(perfluorobutyl)anthracene) obtained in Example 3.

While the present invention has been described in detail and with reference to specific embodiments thereof, it will be apparent to one skilled in the art that various changes and modifications can be made therein without departing from the spirit and scope thereof. The present application is based on Japanese Patent Application (No. 2012-033156) filed on Feb. 17, 2012, and the contents thereof are incorporated herein by reference.

Industrial Applicability

The present invention provides a fluorine-containing aromatic compound applicable to both of a dry process and a wet process and expectable to have high carrier mobility.

By introducing a fluorine-containing alkyl group by using an acene that is a condensed aromatic ring compound as a core skeleton without using a metal coupling reaction, solubilization in a low polar solvent and decrease in contamination with heavy metals are achieved, so that there can be obtained a fluorine-containing aromatic compound having high carrier mobility.

Owing to the improvement in solubility in an organic solvent by the introduction of the fluorine-containing alkyl group and the improvement in the high carrier mobility by the fluorine atom, an organic semiconductor material containing the compound can be utilized in organic EL elements for next-generation flat panel displays, organic thin-film solar batteries as light-weight and flexible power sources, organic thin-film transistors, and the like.

The invention claimed is:

1. A method comprising:
   reacting a compound represented by the following formula (1) with a compound represented by the formula Rf$_1$X$_1$ in a halogen-containing solvent in the presence of a thiosulfate salt under light irradiation; and
   heating a resultant obtained in the reacting step,
   thereby obtaining a fluorine-containing aromatic compound represented by the following formula (2-1):

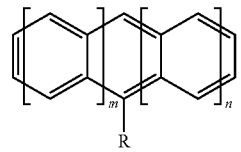

(1)

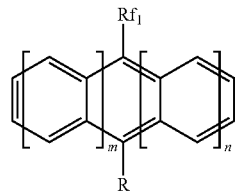

(2-1)

[R is a hydrogen atom, an alkyl group having a carbon number of 2 to 12 which may have a substituent other than a fluorine atom, or a monovalent aromatic group which may have a substituent;
Rf$_1$ is a fluorine-containing alkyl group having a carbon number of 1 to 12 which may have a substituent;
X$_1$ represents an iodine atom or a bromine atom; and
m is an integer of 1 or more, n is an integer of 0 or more and m+n is an integer of 1 or more and 5 or less].

2. The method according to claim 1, wherein R is a hydrogen atom or an unsubstituted alkyl group having a carbon number of 2 to 12.

3. The method according to claim 1, wherein in the formula (2-1), Rf$_1$ is a perfluoroalkyl group having a carbon number of 1 to 6.

4. The method according to claim 1, wherein the compound represented by the formula (2-1) is a compound represented by the following formula (3-1):

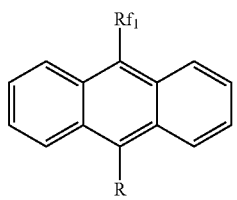

(3-1)

[$Rf_1$ and R represent the same meanings as mentioned above].

5. The method according to claim 1, wherein the compound represented by the formula (2-1) is a compound represented by the following formula (4-1):

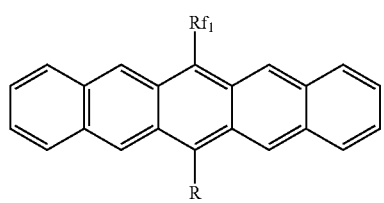

(4-1)

[$Rf_1$ and R represent the same meanings as mentioned above].

6. The method according to claim 1, wherein the wavelength of the irradiation light is from 300 to 600 nm.

7. The method according to claim 1, wherein the heating temperature is from 200 to 300° C.

8. A method comprising:
obtaining the compound represented by the following formula (2-1) by the method as defined in claim 1; and
obtaining an organic semiconductor material comprising the compound represented by the following formula (2-1),
wherein contents of metals of Ni, Cu, Zn, and Pd in the organic semiconductor material are each 1 ppm by mass or less and total content of metals in the organic semiconductor material is 10 ppm by mass or less:

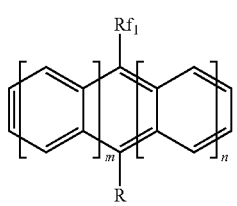

(2-1)

[$Rf_1$, R, m and n represent the same meanings as mentioned above].

9. A method comprising:
reacting a compound represented by the following formula (1-1) with a compound represented by the formula $Rf_1X_1$ in a halogen-containing solvent in the presence of a thiosulfate salt under light irradiation to obtain a compound represented by the following formula (1-1');
heating the compound represented by the formula (1-1') to obtain a fluorine-containing aromatic compound represented by the following formula (2-1-1);
reacting the compound represented by the formula (2-1-1) with a compound represented by the formula $Rf_2X_2$ in a halogen-containing solvent in the presence of a thiosulfate salt under light irradiation; and
heating a resultant obtained in the reacting step of the compound represented by the formula (2-1-1), thereby obtaining a fluorine-containing aromatic compound represented by the following formula (2-2):

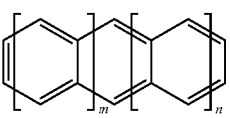

(1-1)

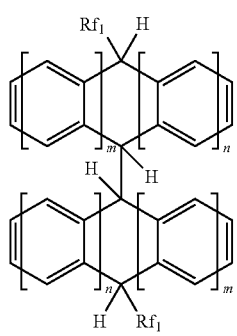

(1-1')

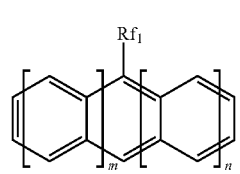

(2-1-1)

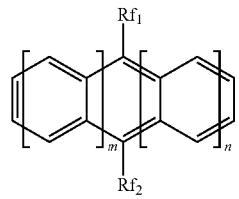

(2-2)

[$Rf_1$ and $Rf_2$ are a fluorine-containing alkyl group having a carbon number of 1 to 12 which may have a substituent and $Rf_1$ and $Rf_2$ may be the same or different;

$X_1$ and $X_2$ represent an iodine atom or a bromine atom and may be the same or different; and m is an integer of 1 or more, n is an integer of 0 or more and m+n is an integer of 1 or more and 5 or less].

10. The method according to claim 9, wherein $Rf_1$ and $Rf_2$ may be the same or different, and $Rf_1$ is a fluorine-containing alkyl group having a carbon number of 1 to 12 which may have a substituent and $Rf_2$ is a fluorine-containing alkyl group having a carbon number of 4 to 7 which may have a substituent.

11. The method according to claim 9, wherein in the formula (2-2), $Rf_1$ and $Rf_2$ may be the same or different, and $Rf_1$ is a perfluoroalkyl group having a carbon number of 1 to 12 and $Rf_2$ is a perfluoroalkyl group having a carbon number of 4 to 7.

12. The method according to claim 9, wherein the compound represented by the formula (2-2) is a compound represented by the following formula (3-2):

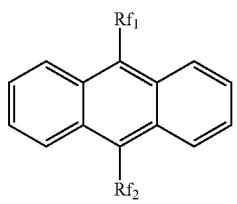

(3-2)

[$Rf_1$ and $Rf_2$ represent the same meanings as mentioned above].

13. The method according to claim 12, wherein in the formula (3-2), $Rf_1$ and $Rf_2$ may be the same or different, and $Rf_1$ is a perfluoroalkyl group having a carbon number of 1 to 12 and $Rf_2$ is a perfluoroalkyl group having a carbon number of 4 to 7.

14. The method according to claim 9, wherein the compound represented by the formula (2-2) is a compound represented by the following formula (4-2):

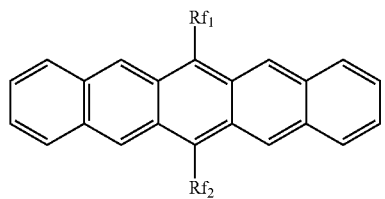

(4-2)

[$Rf_1$ and $Rf_2$ represent the same meanings as mentioned above].

15. The method according to claim 14, wherein in the formula (4-2), $Rf_1$ and $Rf_2$ may be the same or different, and $Rf_1$ is a perfluoroalkyl group having a carbon number of 4 to 7 and $Rf_2$ is a perfluoroalkyl group having a carbon number of 1 to 12.

16. The method according to claim 9, wherein the wavelength of the irradiation light is from 300 to 600 nm.

17. The method according to claim 9, wherein the heating temperature is from 200 to 300° C.

18. A method comprising:
    obtaining the compound represented by the following formula (2-2) by the method as defined in claim 9; and
    obtaining an organic semiconductor material comprising the compound represented by the following formula (2-2),
    wherein contents of metals of Ni, Cu, Zn, and Pd in the organic semiconductor material are each 1 ppm by mass or less and total content of metals in the organic semiconductor material is 10 ppm by mass or less:

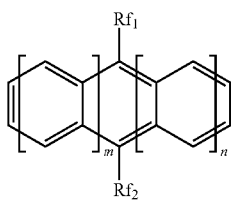

(2-2)

[$Rf_1$, $Rf_2$, m and n represent the same meanings as mentioned above].

* * * * *